US00PP22491P2

(12) United States Plant Patent
Smith

(10) Patent No.: US PP22,491 P2
(45) Date of Patent: Feb. 7, 2012

(54) ***SALVIA* PLANT NAMED 'BRIGHT EYES'**

(50) Latin Name: *Salvia hybrida*
Varietal Denomination: Bright Eyes

(75) Inventor: M. Nevin Smith, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/805,669

(22) Filed: Aug. 12, 2010

(51) Int. Cl.
*A01H 5/00* (2006.01)

(52) U.S. Cl. ..... Plt./475
(58) Field of Classification Search ..... Plt./475
See application file for complete search history.

*Primary Examiner* — June Hwu
(74) *Attorney, Agent, or Firm* — Buchanan Ingersoll & Rooney PC

(57) ABSTRACT

A new and distinct *Salvia* plant of unknown parentage is provided that was discovered in a nursery setting while growing among other *Salvia* plants. Over a long blooming season attractive bi-colored blossoms are formed that are red with a white eye. The growth habit is upright and bushy. The foliage is large and bright green in coloration. Following pruning, the plant displays a tendency to vigorously regrow. The plant is well suited for providing attractive ornamentation.

1 Drawing Sheet

Botanical/commercial classification: *Salvia hybrida/ Salvia* Plant.
Varietal denomination: cv. Bright Eyes.

SUMMARY OF THE INVENTION

The new *Salvia* cultivar of the present invention was discovered during August or September, 2006, while growing in a plant nursery setting among other *Salvia* plants at Watsonville, Calif., U.S.A. The new cultivar is of unknown parentage and likely includes *Salvia microphylla* in its ancestry. The new plant was distinguished from other *Salvia* plants growing in the nursery where it was discovered primarily through a study of its distinctive bi-colored blossoms combined with other attractive botanical characteristics identified hereafter. Had the single plant of the present invention not been discovered and carefully preserved, it would have been lost to mankind.

The plant is a perennial that can be grown to advantage without protection in U.S.D.A. Hardiness Zone Nos. 7 to 11.

It was found that the new *Salvia* cultivar possesses the following combination of characteristics:

(a) displays an upright and bushy growth habit,
(b) forms in abundance over a long blooming season attractive bi-colored red blossoms with a white eye,
(c) displays vigorous large bright green foliage,
(d) displays a tendency to vigorously regrow following pruning, and
(e) is well suited for providing attractive ornamentation.

The new cultivar of the present invention can be readily distinguished from other *Salvia* cultivars, such as the 'Hot Lips' and 'Maraschino' cultivars (both non-patented in the United States). While the 'Hot Lips' cultivar forms bi-colored red and white blossoms, the white blossom marking is not present solely as an eye as in the new cultivar. The blossoms of the 'Maraschino' cultivar are solid red and are lacking a white eye.

The new cultivar well meets the needs of the horticultural industry and can be grown to advantage as attractive ornamentation in parks, gardens, public areas, and residential landscapes.

The new cultivar has been asexually reproduced by the rooting of cuttings for several generations. Such asexual reproduction as performed at Watsonville, Calif., U.S.A., and near West Grove, Pa., U.S.A., has demonstrated that the characteristics of the new cultivar are firmly fixed and stable and are strictly transmissible from one generation to another. Accordingly, the new cultivar asexually reproduces in a true-to-type manner from one generation to another.

The new cultivar has been named 'Bright Eyes'.

BRIEF DESCRIPTION OF THE PHOTOGRAPH

The accompanying photograph shows as nearly true as it is reasonably possible to make the same, in a color illustration of this character, a close view of typical specimens of the new cultivar while growing outdoors. The bi-colored red blossoms with a white eye are illustrated as is the large bright green foliage. The plants had been reproduced by the rooting of cuttings in a greenhouse and subsequently had been transplanted to the outdoors near West Grove, Pa., U.S.A. The photograph was obtained during July 2010 when the plants were approximately one year of age.

DETAILED DESCRIPTION

The chart used in the identification of colors is that of The Royal Horticultural Society (R.H.S. Colour Chart-1995) of London, England. Color terminology in common terms sometimes is included as an aid to the reader. Such color terminology is to be accorded its customary dictionary significance. The description is based on the observation of typical specimens of the new cultivar at an age of approximately one year during July 2010 while growing outdoors near West Grove, Pa., U.S.A.

Plant:

*Form.*—Bushy, vigorous, and generally upright.
*Height.*—Commonly up to approximately 45 cm on average.
*Width.*—Commonly approximately 60 cm on average.

*Growth habit.*—Perennial in U.S.D.A. Hardiness Zone Nos. 7 to 11.
*Leaf arrangement.*—Opposite.
*Leaf configuration.*—Elliptic to oblong.
*leaf length.*—Commonly approximately 3 to 3.5 cm on average.
*Leaf width.*—Commonly approximately 2 to 3 cm on average.
*Leaf margin.*—Repand.
*Leaf texture.*—Commonly slightly fleshy.
*Leaf blade color.*—Green Group 137C on the upper surface, and Green Group 138B on the under surface.
*Leaf blade apex.*—Acute to obtusely rounded.
*Leaf blade base.*—Mainly obtuse.
*Scent.*—Leaves commonly display a tangy fruity scent when crushed.
*Petiole shape.*—Somewhat flattened.
*Petiole length.*—Variable and commonly approximately 5 to 9 mm.
*Petiole width.*—Commonly approximately 1 to 1.5 mm.
*Petiole texture.*—Smooth.
*Petiole color.*—Yellow-Green Group 145A.

Inflorescence:
*Time.*—Prolonged blooming period beginning in May and extending into September.
*Bud shape.*—Oblanceolate.
*Bud size.*—Approximately 1 cm.
*Bud color.*—Yellow-Green Group 145A overlaid with Black Group 202A.
*Type.*—Terminal raceme.
*Diameter.*—Commonly approximately 1.6 cm for an individual flower on average and approximately 5.5 cm for a terminal raceme at the widest point including the width of the lower lip on average.
*Length.*—Commonly approximately 3 cm for an individual flower on average, and approximately 15 to 20 cm for a terminal raceme on average.
*Number.*—Commonly up to approximately 50 flowers per plant on average.
*Configuration.*—Tubular, and two-lipped.
*Pedicel length.*—Commonly approximately 3 to 4 mm on average.
*Pedicel width.*—Commonly approximately 2 mm on average.
*Pedicel color.*—Green, Yellow-Green Group 145B.
*Calyx shape.*—Broadly campanulate and flared towards the apex.
*Calyx rib number.*—Commonly 13 and longitudinally disposed.
*Calyx length.*—Commonly approximately 10 mm on average.
*Calyx width.*—Commonly up to 6 mm.
*Calyx texture.*—Glandular and puberulent on the upper and under surfaces.
*Calyx color.*—On the upper lobe Red-Purple Group 60B at the apex and Yellow-Green Group 145A at the base, and on the lower lobes primarily Yellow-Green Group 145B.
*Calyx lobe number.*—3.
*Calyx upper lobe number.*—1.
*Calyx upper lobe shape.*—Acute.
*Calyx upper lobe length.*—Commonly approximately 4 mm on average.
*Calyx upper lobe width.*—Commonly approximately 4 mm in width.
*Calyx lower lobe number.*—2.
*Calyx lower lobe shape.*—Acute.
*Calyx lower lobe length.*—Commonly approximately 3 mm on average.
*Calyx lower lobe width.*—Commonly approximately 4 mm on average.
*Corolla shape.*—Tubular proximally to two-lipped distally.
*Corolla length.*—Commonly approximately 2.2 to 2.5 cm on average.
*Corolla diameter.*—Approximately 0.5 cm.
*Corolla color.*—The base commonly is near Yellow-White Group 158D, the tube is near Red-Purple Group 61B, the upper lip is near Red-Purple Group 60A, the lower lip is near Red Group 53B, and the inner corolla tube commonly is a blend of Red-Purple Group 60A and White Group 155B. The blossoms display a white eye, near White Group 155B, as shown in the photograph.
*Corolla tube length.*—Approximately 23 mm on average.
*Corolla tube width.*—Approximately 3 mm on average.
*Corolla tube depth.*—Approximately 7 mm on average.
*Corolla tube lip number.*—2.
*Corolla upper lip number.*—1.
*Corolla upper lip shape.*—Hood-like.
*Corolla upper lip length.*—Commonly approximately 9 mm average.
*Corolla lower lip length.*—2, suborbicular.
*Corolla lower lip shape.*—Banner-like, and extended downward.
*Corolla lower lip outline.*—Obovate.
*Corolla lower lip length.*—Commonly approximately 12 mm on average.
*Corolla lower lip diameter at tip.*—Approximately 12 mm on average.
*Pistil number.*—1.
*Style length.*—Approximately 2.5 cm on average.
*Style width.*—Commonly approximately 1 mm on average.
*Style attachment site.*—At four-lobed ovary between lobes.
*Stamen number.*—2.
*Stamen shape.*—Seesaw-like.
*Filament length.*—Approximately 6 mm on average.
*Connective length.*—Approximately 12 mm on average.
*Anther length.*—Approximately 2 mm on average.
*Anther diameter.*—Approximately 1 mm on average.
*Anther color.*—Yellow-Orange Group 16A.
*Anther attachment site.*—At outer end of the connective.
*Fruit.*—None observed during observations to date.

Development:
*Vegetation.*—Vigorous and displays a tendency to quickly regrow following pruning.
*Blooming.*—Displays long blooming season.
*Fertility.*—Not observed with the plants being sterile during observations to date.
*Winter hardiness.*—The plant is a perennial that can be grown in at least U.S.D.A. Hardiness Zone Nos. 7 to 11.
*Disease resistance.*—No particular sensitivity to disease has been encountered during observations to date.

I claim:

1. A new and distinct *Salvia* plant characterized by the following combination of characteristics:

(a) displays an upright and bushy growth habit, (b) forms in abundance over a long blooming season attractive bi-colored red blossoms with a white eye, (c) displays vigorous large bright green foliage, (d) displays a tendency to vigorously regrow following pruning, and (e) is well suited for providing attractive ornamentation; substantially as illustrated and described.

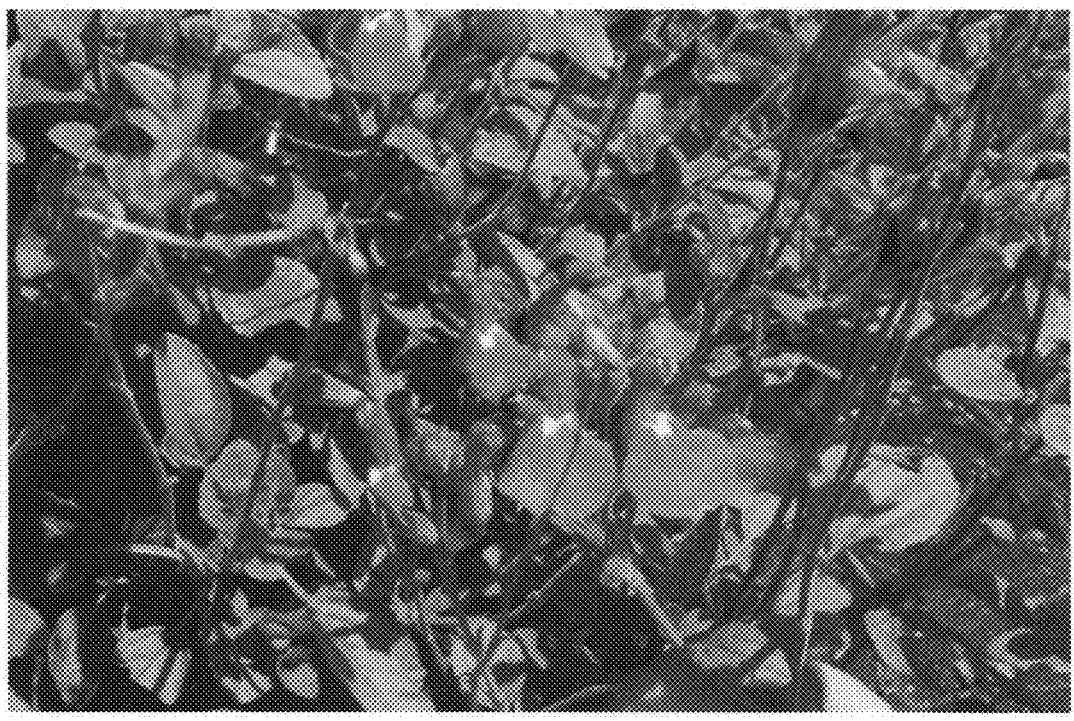

* * * * *